United States Patent [19]

Yardley

[11] 4,233,990
[45] Nov. 18, 1980

[54] VOLUME AND FLOW-RATE DEPENDENT INSPIRATOR

[75] Inventor: Lloyd M. Yardley, Decatur, Ga.

[73] Assignee: Empire Plastics Manufacturing Inc., Decatur, Ga.

[21] Appl. No.: 22,330

[22] Filed: Mar. 20, 1979

[51] Int. Cl.³ .................... A61M 16/00; A63B 23/00
[52] U.S. Cl. ...................................... 128/728; 272/99
[58] Field of Search .............. 128/727, 728; 272/130, 272/99, 93, DIG. 0.005

[56] References Cited

U.S. PATENT DOCUMENTS

| 793,177 | 6/1905 | Cady | 272/99 X |
|---|---|---|---|
| 3,395,699 | 8/1968 | Beasley | 128/728 |
| 3,669,097 | 6/1972 | Fitz | 128/728 |
| 3,754,546 | 8/1973 | Cooper | 272/99 X |
| 3,875,626 | 4/1975 | Tysk et al. | 128/728 |
| 4,096,855 | 6/1978 | Fleury | 272/99 X |
| 4,171,804 | 10/1979 | Thead | 128/727 X |

FOREIGN PATENT DOCUMENTS 685815 1/1953 United Kingdom ...................... 272/99

*Primary Examiner*—George J. Marlo
*Attorney, Agent, or Firm*—Fleit & Jacobson

[57] ABSTRACT

A pulmonary exercising device having a first mode of operation in which the device provides a visual indication of the volume of inspired air and a second, subsequent mode of operation in which the device provides a visual indication of the rate of inspiration of air. The device has an axially-extending housing with a side wall sealed to a base member. A hollow tubular member surrounds an opening formed in the center of the base and extends axially to the top of the housing. A bellows is positioned within the housing and has its bottom portion sealed to peripheral portions of the base. A bushing is positioned in a central, top portion of the bellows so that the bellows is able to move up and down on the tubular member. The interior of the bellows forms a first chamber within the housing, with the remaining portion of the housing forming a second chamber. An opening is formed in an upper portion of the tubular member so that a user of the device is able to withdraw air from the second chamber through the tubular member, a channelway associated with the opening formed in the center of the base, and tubing extending between the channelway and user. Openings formed in the base communicate the interior of the bellows with the ambient environment. The length of the bushing is less than the length of the opening formed in the tubular member so that the opening communicates with the interior of the bellows, or first chamber, after the bottom of the bushing passes the bottom of the opening.

15 Claims, 9 Drawing Figures

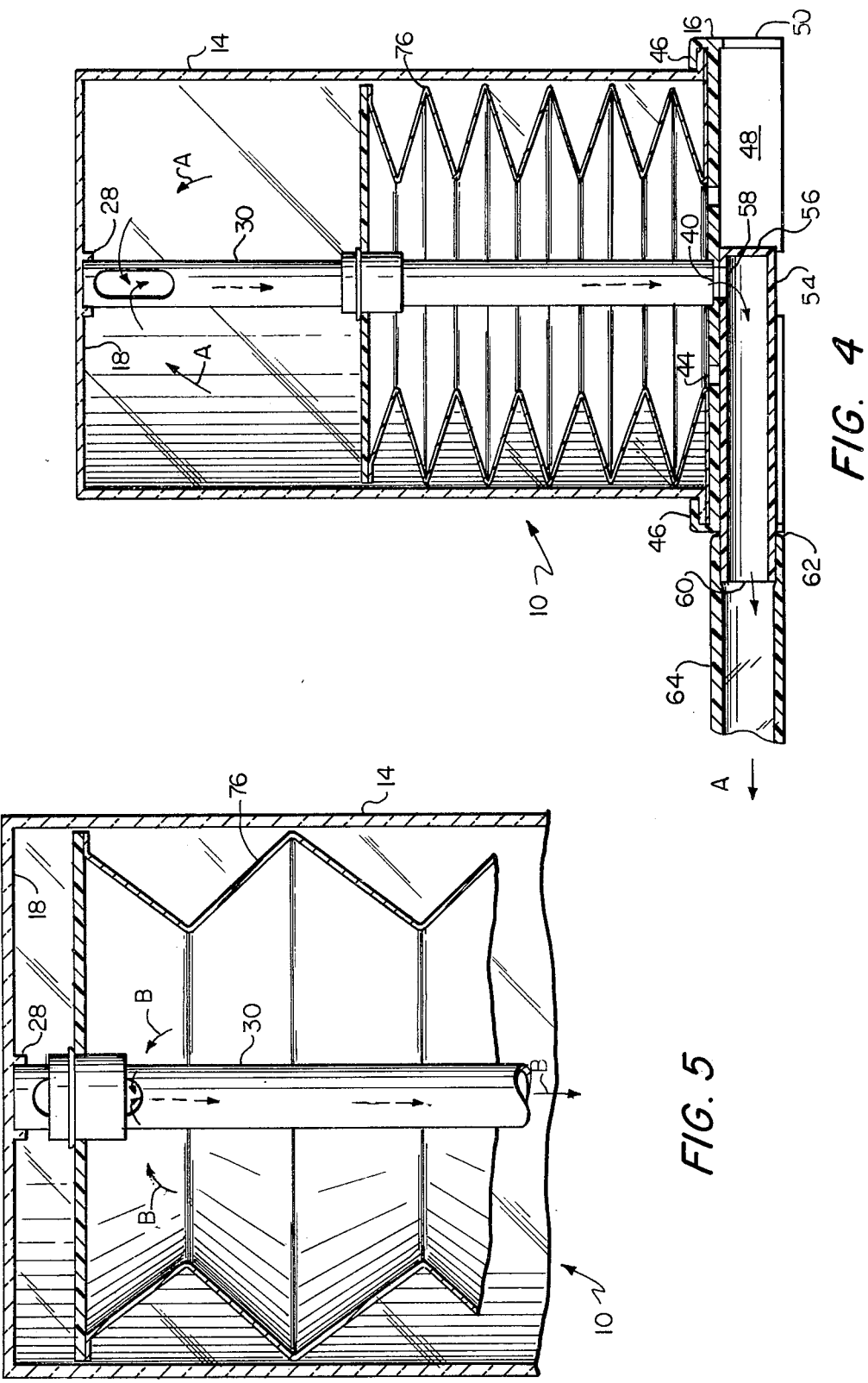

VOLUME AND FLOW-RATE DEPENDENT INSPIRATOR

BACKGROUND OF THE INVENTION

1. Field of the Invention

This invention relates to a respiration exercising device and, in particular, to a device for enhancing inspiration for improvement of pulmonary performance. More specifically, this invention relates to a respiration exercising device that, in a first mode of operation, operates as a volume measuring device, and, in a subsequent mode of operation, operates as a flow-rate dependent device.

2. Description of the Prior Art

One of the main causes for slow recovery of patients following pulmonary operations has been inadequate oxygen exchange in the lungs resulting from shallow breathing accompanying the use of general anesthesia. This condition can lead to partial or complete collapse of the lungs and to pneumonia.

Various methods have been proposed for preventing or minimizing such pulmonary complications, including instructions to the patients to breath deeply, coughing exercises, and the use of blow bottles of the type described in U.S. Pat. No. 3,811,671. In some cases, such methods of blowing exercise have not been successful because alveoli have not been adequately expanded. Accordingly, numerous devices employing positive pressure breathing have been introduced to stimulate a patient to improve his or her inspiratory capacity.

Previously known breath exerciser devices and inspirators are described in British Pat. Nos. 8,662 and 685,815. Also, such devices are described in U.S. Pat. Nos. 471,389, 793,177, 3,635,214, 3,695,608, 3,754,546, 3,822,699, 3,908,987, 3,936,048, 3,811,671, 4,060,074, and 4,025,070.

With the exception of the blow bottle-type exercising device, the previously known devices have not provided any indication of the volumetric capacity of the patient. Since the interior dimensions of previously known devices have been variable, air leakage around the blocking devices used in the devices has limited their usefulness to measure volume.

SUMMARY OF THE INVENTION

It is an object of the present invention to provide an improved respiration exercising device that overcomes the problems encountered with use of previously known devices.

The exercising device of the present invention provides an inspirator that is a volume unit during a first mode of operation and a flow-rate dependent unit during a subsequent mode of operation.

In accordance with the present invention, a pulmonary exercising device is provided having an axially-extending housing attached to a base by sealing side walls of the housing to the base. A hollow tubular member extends coaxially within the housing between the base and the housing top. An axially-extending opening is formed in an upper portion of the tubular portion close to the top. A bushing having a length shorter than that of the opening is slidably positioned on the tubular member. A bellows is positioned inside the housing to define a chamber and has an opening in its upper surface to receive the bushing so that the top of the bellows can move up and down on the tubular member. The bottom of the bellows is sealed to peripheral edges of the base. One or more holes are formed in the base to connect the interior of the bellows to the ambient environment. The interior of the bellows forms a first chamber within the housing, while the portion of the housing exterior of the bellows forms a second chamber. The base of the housing contains an axial opening through which the interior of the tubular member communicates with a channel-way connected to flexible tubing. Inhalation of air through a mouthpiece connected to the flexible tubing draws air from the upper part of the second chamber through the opening in the tubular member, thus reducing air pressure within the second chamber. As the air pressure is reduced, the bellows expands thereby providing a visual indication of the amount of air being withdrawn from the second chamber. Preferably, a sealing member is positioned between the bushing and the tubular member, so that there is little or no air leakage between the two. After the bottom of the bushing passes the bottom of the opening formed in the tubular member, the user is able to draw air mainly from the first chamber. As long as the user is withdrawing air from the housing at a rate sufficient to maintain the bottom of the bushing above the bottom of the opening in the tubular member, a visual indication of the rate of air withdrawal is provided. When the user stops inhaling, the bellows collapses to the bottom of the housing. Preferably, a disc or plate is attached to the top of the bushing to urge it towards its collapsed position.

In one embodiment of the present invention, the side walls of the housing are spaced a constant distance apart, and the peripheral edges of the bellows and plate associated therewith are closely spaced from the side walls so that little, if any, air flow is possible between the side walls of the housing and the peripheral edges. The position of the top of the bellows provides an accurate visual indication of the volumetric amount of air withdrawn from the housing.

In another embodiment of the present invention, the side walls of the housing are slightly tapered. The previously described bellows is positioned inside the housing to provide upper and lower chambers. Since the bellows normally does not permit direct communication between the upper and lower chambers, air leakage between side walls of the housing and the top of the bellows resulting the taper of the side walls, does not create a problem. In effect, the leaked air forms an extended portion of the upper chamber that is coaxially with, surrounds, and is separated from the lower chamber.

The invention, and its objects and advantages, will become more apparent in the detailed description of the preferred embodiments presented below.

BRIEF DESCRIPTION OF THE DRAWINGS

In the detailed description of the preferred embodiments of the invention presented below, reference is made to the accompanying drawings, in which:

FIG. 4 is a cross-sectional view taken along line 4—4 of FIG. 1, slightly modified, illustrating the device being used to measure volume;

FIG. 5 is a partial longitudinal sectional view similar to FIG. 4 illustrating use of the device as a flow-rate dependent unit;

DESCRIPTION OF THE PREFERRED EMBODIMENTS

Figure 1:
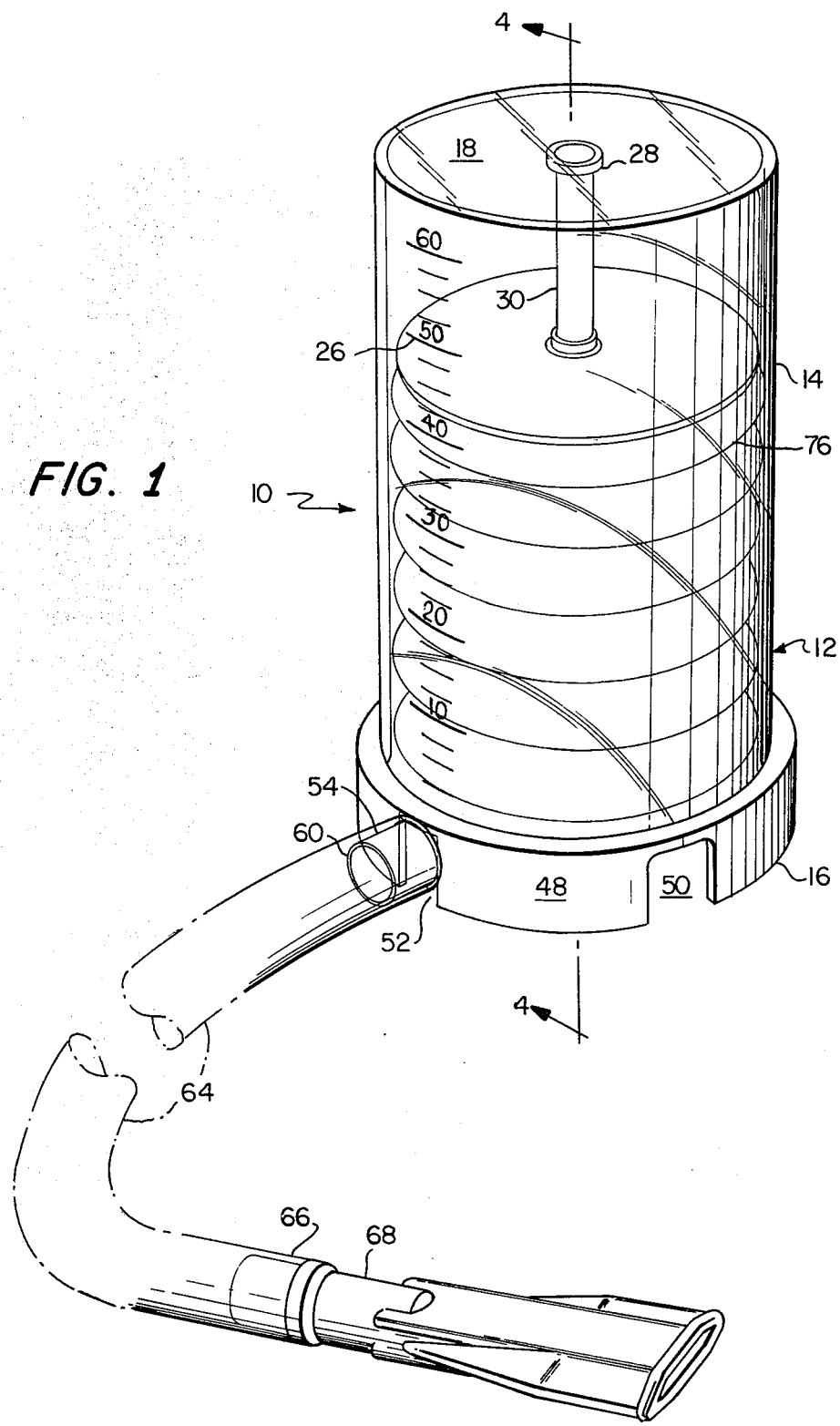
FIG. 1 is a perspective view of a device illustrating one embodiment of the present invention.

Because respiratory exercisers are well known, the present description will be directed, in particular, to elements forming part of, or cooperating more directly with, the present invention. Elements not specifically shown or described herein are understood to be selectable from those known in the art.

Referring now to the drawings, and to FIGS. 1 to 5 in particular, one embodiment of the present invention is illustrated and will be described in connection with a respiratory exerciser, generally designated 10.

The exerciser or exercising device 10 includes a housing, generally designated 12, having a cylindrical container 14 connected to a base 16. The container 14 has a closed end 18 and an open end 20 surrounded by an outwardly flared lip portion 22 of a side wall 24. Preferably, the side wall 24 includes marking indicia 26 to indicate volumetric changes within the container 14.

Figure 2:
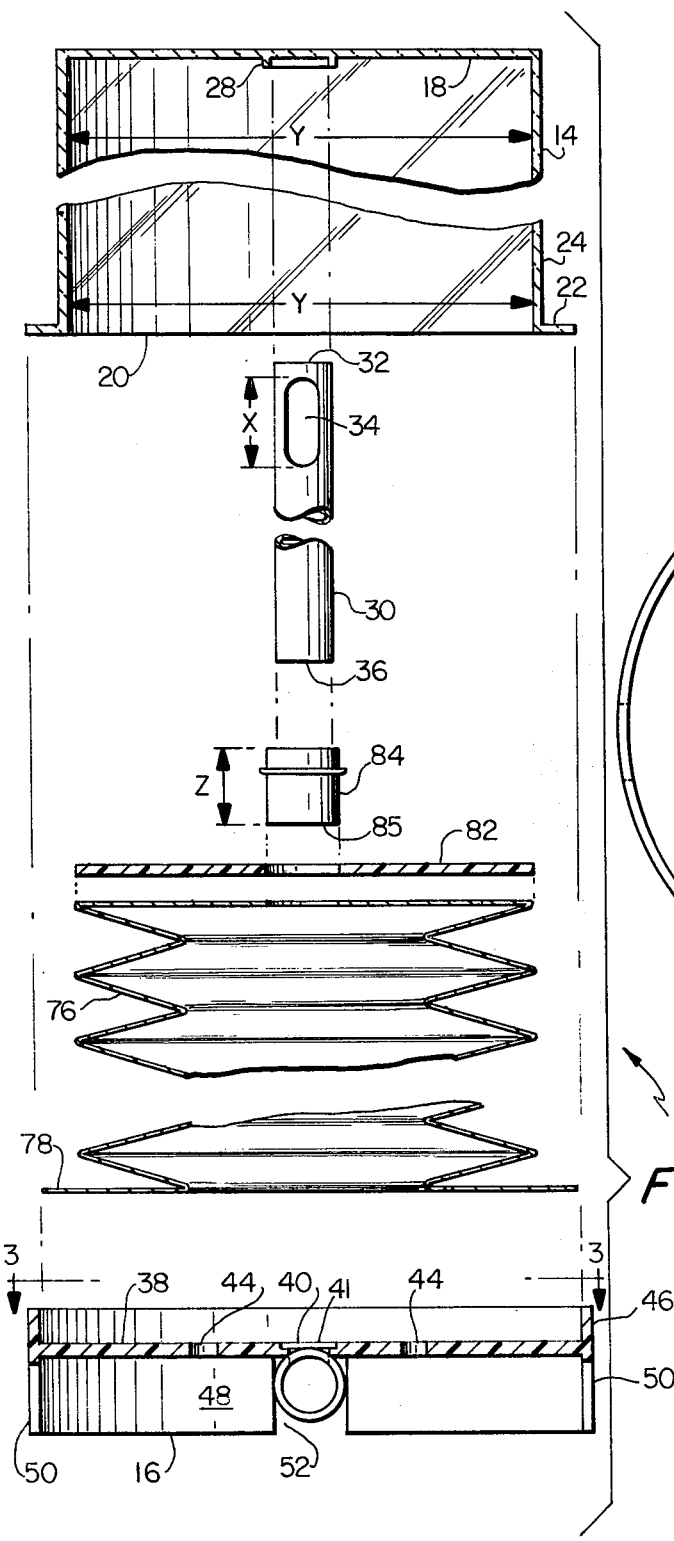
FIG. 2 is an exploded perspective view of the device illustrated in FIG. 1.
Figure 3:
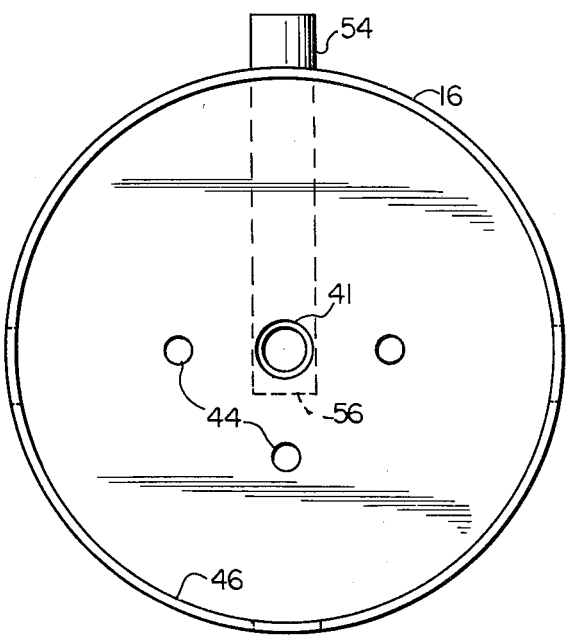
FIG. 3 is a view along line 3—3 of FIG. 2.

A collar 28 is formed integral with or attached to a central portion of the inside of closed end 18. A hollow tube or slide rod 30 has one end 32 mating with the collar 28. It will be appreciated that end 32 can either be inserted into collar 28, as illustrated, or surround collar 28. A longitudinally-extending opening 34 having a length "X" is formed in tube 30 close to end 32. The opening 34 can terminate before end 32, as illustrated in FIG. 2, or can extend all the way to end 32. The other end 36 of tube 30 is connected to the top surface 38 of base 16 and surrounds an opening or passageway 40 formed in the base. Preferably, a portion 41 of top surface 38 is cut away or stepped to define a step for sealingly receiving end 36.

Top surface 38 of base 16 also includes one or more openings or passageways 44 spaced from tube 30 and the opening 40. A peripheral collar 46 extends upwardly from an outer portion of top surface 38. A downwardly extending side wall 48 or a plurality of feet are provided to space the top surface 38 from a surface supporting the exercising device 10. One or more openings 50 are formed in the side wall 48 to connect openings 44 with the ambient environment. Also, an opening 52 is provided in the side wall that communicates with a channelway or tubular member 54 that is preferably connected to the bottom of top surface 38. The channelway 54 extends past opening 40 and terminates in a closed end 56 positioned near the opening 40. An opening 58 is formed in the channelway that aligns with opening 40 to establish communication between the interior of the channelway and the interior of slide rod 30. The other end 60 of the channelway is adapted to receive one end 62 of a conduit or tubular member 64. End 62 is either inserted into or surrounds end 60 of channelway 54. The other end 66 of member 64 is either connected to or shaped to form a mouthpiece 68.

Figure 9:
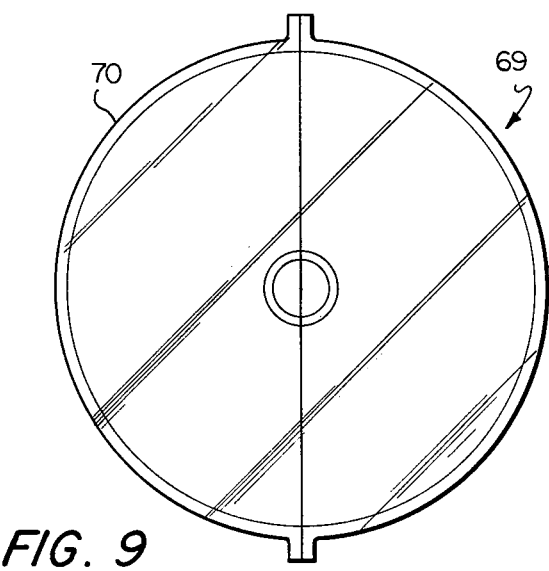
FIG. 9 is a top view of a still further embodiment of the present invention.

Preferably, the inside diameter "Y" of the container 14 is the same at both the top and the bottom of the container. A suitable method for producing a container without taper, i.e., with straight sides, is described in an article by Paul M. Coffman, entitled "Stretch-forming: a simple process with a lot of potential", published in the August, 1977, issue of *Plastics Engineering*. Another suitable method, as schematically illustrated in the embodiment of FIG. 9, involves forming a container, which is generally designated 69, from two moulded semi-cylindrical members 70 and 72. Container 69 performs the same function as container 14 of the embodiment illustrated in FIGS. 1-5. By using moulds, the problems encountered with changes in diameter during extruding plastic members are avoided.

Since the bellows provides two separate chambers within the housing, a presently preferred embodiment utilizes an injection molded container having slightly tapered sides, for instance, a taper angle or draft between about 1° and 3°, preferably approximately 2°.

Referring again to FIGS. 1, 2, 4, and 5, a bellows 76 is positioned within the housing 12. The bellows 76, is manufactured using the method described in the aforementioned article or by any other suitable method, such as blow molding. The bellows has an outwardly flared lip portion 78 surrounding an open end of the bellows. The outside diameter of the bellows is slightly less than, preferably between 0.001 and 0.005 inches, the inside diameter "Y" of the container 14. The bellows can have either straight or tapered side walls, with the maximum diameter being such that there is always clearance between the bellows and the walls of the container. The inside diameter of the bellows is selected such that the convolutions of the bellows do not block the openings 44 formed in the base 16. A wafer or disc 82 is attached to the top of bellows 76, as illustrated in FIG. 2, or is positioned inside the top of the bellows. Alternatively, as illustrated in FIGS. 4 and 5, the plate member or disc 82 forms the top of the bellows. The disc 82 is provided to urge the bellows towards a collapsed position. Both the bellows 76 and disc 82 contain openings for receiving a bushing 84. The bushing 84 has an inside diameter slightly larger than the outside diameter of slide rod 30 so that the disc and bushing can move up and down on the slide rod. In the embodiment of the present invention illustrated in FIGS. 6 and 7, a sealing member 85 is provided to prevent escape of air between the outside of the rod and the inside of the bushing. As illustrated in FIG. 2, the axial length "Z" of bushing 84 is less than the length "X" of opening 34.

Referring now to FIG. 2, assembly of the exercising device 10 will be described. First, disc 82 and bellows 76 are connected to bushing 84. Then, rod 30 is inserted through bushing 84 and centered on or in collar 28. Base 16 is then moved towards container 14 in such manner that end 36 of rod 30 surrounds opening 40 and is seated in stepped portion 41 of surface 38. Also, lip portion 78 of bellows 76 and lip portion 22 of container 14 are positioned inside collar 46. Lip portions 22 and 78 are sealed in an air-tight manner to top surface 38 by sonic welding, glueing, heating, spin welding, or other suitable methods. Alternatively, or in addition, collar 46 is deformed, as illustrated in FIG. 4, to obtain the required seal. Preferably the clearance between end 36 and portion 41 is such that an air-tight friction seal is obtained between the two when the container is sealed to the base. End 62 of tubing member 64 is then connected to end 60 of channelway 54. Device 10 is then ready for use.

In use, a user of the device or patient inhales through mouthpiece 68 to create a vacuum or reduced pressure in an upper portion or chamber of container 14. As illustrated by the arrows "A" in FIG. 4, air flows from the upper chamber, through tubular members 30 and 64 to the user. Since the interior of bellows 76 defines a second chamber that communicates with the atmosphere through openings 44 and 50, the reduction of pressure within the upper portion of container 14 caused by inhalation by the user results in expansion and upward movement of the bellows. The extent of upward movement is measured by using the indicia 26 on the side wall 24. Continued evacuation of container 14 results in upward movement of the bellows into the position illustrated in FIG. 5. In this position, the device 10 operates as a flow-rate dependent device. Since the length "Z" of the bushing 84 is less than the length "X" of opening 34, the user is able to inhale atmospheric air through an air path extending from openings 50, openings 44, through the interior of bellows 76, the bottom of opening 34, through the interior of rod 30, opening 40, opening 58, through the interior of channelway 54, and through the interior of tubing 64. Part of this path is schematically illustrated by the arrows "B" in FIG. 5. Since the user is able to inhale atmospheric air from the lower chamber through the bottom of opening 34, the possibility of the user encountering a sudden back pressure when the upper chamber is totally evacuated is eliminated.

Upon completion of a breathing exercise, the combined weight of disc 82 and the bellows returns the bellows 76 to the bottom of container 14.

Since the interior diameter of container 14 is constant, it is easy to measure the amount of air withdrawn from the container. Even when the interior diameter is tapered between approximately 1° and 3°, it is still easy to measure withdrawn air because the bellows divides the interior of the container into separated portions. Thus, air flow variations resulting from changes in the gap between the walls 14 and edges of disc 82 have little or no effect on the rate of movement of bellows 76. In an embodiment of the present invention intended for adult use, the volume of the container is approximately 2.6 liters. In another embodiment primarily intended for pediatric use, the volume of the container is approximately 1.5 liters. It will be appreciated that other volumes can be used, depending on the needs of a particular user. One embodiment of the device illustrated in FIGS. 1 to 5 utilizes a container 14 having an inside diameter of approximately 5.750 inches and an exterior diameter of approximately 5.870 inches. The height of container 14 is approximately 1.6 times its diameter. Both the disc 82 and bellows 76 have outside diameters of approximately 5.748 inches. The outside diameter of the base is approximately 6.5 inches, with collar 46 being approximately 0.25 inches wide. It will be appreciated that these dimensions are merely illustrative of one embodiment of the present invention.

Figure 6:
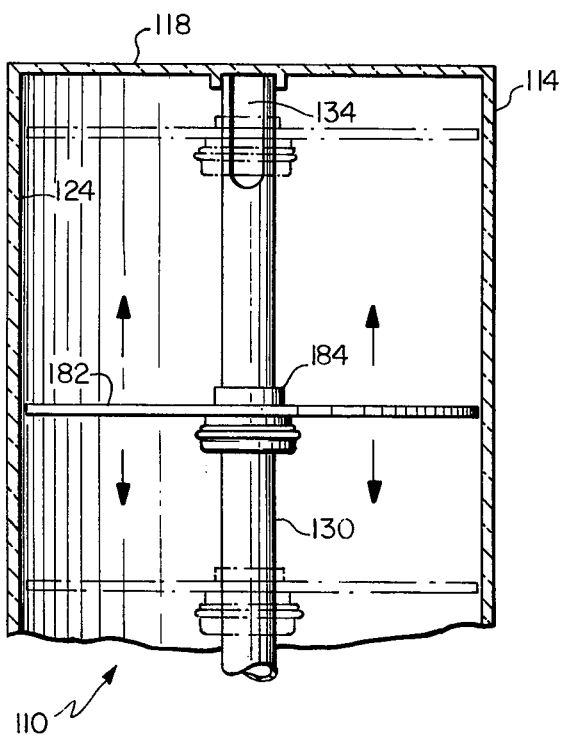
FIG. 6 is a view similar to FIG. 4 illustrating another embodiment of the present invention.

Referring now to FIG. 6, another embodiment of the present invention is illustrated.

Since the embodiment illustrated in FIG. 6 is similar to that previously described in connection with FIGS. 1 to 5, the same reference numerals, preceded by the numeral "1", have been used to identify the illustrated components. The device illustrated in FIG. 6, which is generally designated 110, has a housing 112 formed by connecting a cylindrical container 114 to a base (not illustrated). A hollow tube or slide rod 130 extends between the top 118 of container 114 and the top surface of the base. A disc 182 is positioned on rod 130 to divide the interior of container 114 into upper and lower chambers. Since the interior diameter of container 114 is constant, the edges of disc 182 can be spaced close enough to the interior of sidewall 124 that air passage between the two members is extremely small. Also, the rate of leakage does not vary with the vertical position of the disc. Thus, the device illustrated in FIG. 6 is able to operate as a volume unit without the bellows used with the embodiment illustrated in FIGS. 1 to 5. It should be noted, however, that use of a bellows is preferred because the bellows reduces the criticality of manufacturing tolerances and virtually eliminates all air leakage.

As with the previously discussed embodiment, a bushing 184 cooperates with an opening 134 in rod 130 to prevent cut-off of air and a sudden back pressure when the container 114 is evacuated during use. The opening 134 extends to the top of the rod, as illustrated in FIG. 6. It will also be appreciated that the opening can terminate short of the rod end in a manner similar to opening 34 illustrated in FIG. 2. Alternatively, the disc and bushing are formed as an integral unit.

It will be readily apparent that use of the embodiment of FIG. 6 is substantially the same as use of the embodiment previously described in conjunction with FIGS. 1 to 5.

Figure 7:
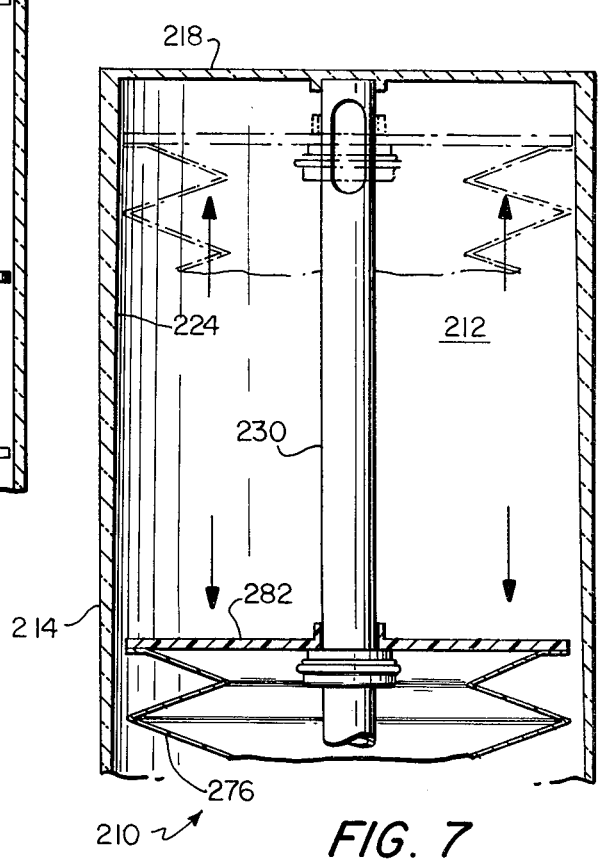
FIG. 7 is a view similar to FIG. 4 of still another embodiment of the present invention.

Referring now to FIG. 7, another embodiment of the present invention is illustrated. Since this embodiment is similar to the embodiment previously described in connection with FIGS. 1 to 5, the same reference numerals, preceeded by the numeral "2", have been used to identify the components of this embodiment.

As illustrated in FIG. 7, an exercising device, which is generally designated 210, has a housing 212 formed by connecting a cylindrical container 214 to a base (not shown). A hollow tube 230 extends between the top 218 of container 214 and the top surface of the base. A bellows 276 is centered on the rod 230 and has one end sealed to the top surface of the base radially outside of openings or passageways extending through the top surface of the base. A plate or disc 282 is attached to or forms the other end of the bellows. With this embodiment, a cylindrical container 214 is used having a varying internal diameter, for instance, a draft or taper between approximately 1° and 3°. Thus, the outside diameter of the bellows 276 and disc 282 are selected in such a manner that there is always at least a minimum clearance between these members and the interior of side wall 224. Although air can pass between the top of bellows 276 and side wall 224, this is not objectionable because side wall 224 is sealed in an air-tight manner to the base, and bellows 276 prevents escape of air through the openings formed in the base.

It will be appreciated that with this embodiment it might be more difficult to accurately measure the amount of air withdrawn by a user of the device 210; however, this embodiment is presently preferred because producing a perfectly straight-walled container with present technology is difficult and costly. Also, it should be readily apparent that use of the device 210 is similar to use of the previously described device 10.

Figure 8:
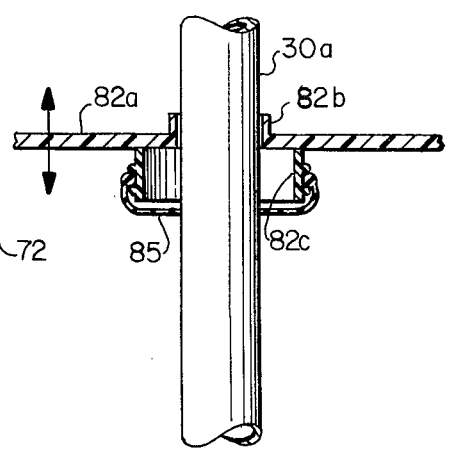
FIG. 8 is an enlarged perspective view of one component of the embodiments illustrated in FIGS. 6 and 7.

As previously discussed, the embodiments illustrated in FIGS. 6 and 7 use a sealing member 85 of the type illustrated in FIG. 8. Since the structure illustrated in FIG. 8 can be used with any of the embodiments illustrated in FIGS. 1 to 7, the reference numerals used with FIG. 1, followed by the letter "a", will be used to describe illustrated components.

Referring now to FIG. 8, a portion of an exercising device, generally designated 10a, is illustrated having a rod 30a passing through a central aperture formed in a member 82a. The member 82a is positionable within a housing (not shown) for reciprocating movement in a vertical direction. The member 82a is a disc attached to the top of a bellows (not shown), either on the inside or outside of the bellows. Alternatively, member 82a forms the top of the bellows. A portion of the member 82a, designated 82b, forms a first cylindrical collar that is spaced from and acts as a guide surface for the rod 30a. It will be appreciated that collar 82b can extend upwards, as illustrated, downwards, or both upwards and downwards.

Since the collar 82b is spaced from rod 30a, there is a possibility of undesired air leakage between upper and lower chambers defined by the member 82a. In order to eliminate this possibility, a second cylindrical collar, designated 82c, is formed integral with or attached to member 82a. A portion of the exterior wall of collar 82c is shaped to define a seat for receiving the sealing member 85. The shaped portion can be either a recessed or a protruding portion. The sealing member 85 is formed of latex or similar material and has a peripheral beaded portion resiliently held in the shaped portion of collar 82c. The center of member 85 is formed with a passageway that has the same or slightly smaller size than the diameter of rod 30a. Thus, member 85 slidingly engages rod 30a during vertical movement of member 82a, thereby preventing air leakage through the opening in member 82a that receives rod 30a. It will be appreciated that portions 82b and 82c can be combined into one cylindrical collar, if desired.

Although all of the illustrated embodiments have a generally cylindrical shape, it will be appreciated that other shapes, such as elliptical and rectangular can be used with the present invention. Similarly, the slide rod and channelway can have other shapes than those illustrated. Modification of the aforementioned members will require corresponding modification of the components interacting with the modified members.

The invention has been described in detail with particular reference to preferred embodiments thereof, but it will be understood that variations and modifications can be effected within the spirit and scope of the invention.

What is claimed is:

1. A device for measuring inspiratory capacity comprising:
    a housing;
    dividing means positioned inside said housing for dividing the interior of said housing into a first chamber and a second chamber, at least a portion of the second chamber being positioned above the first chamber;
    first means for establishing fluid communication between the first chamber and the ambient environment;
    second means for establishing fluid communication between the second chamber and a user of the device so that inhalation by the user through the second means creates a negative pressure within the second chamber;
    said dividing means including means responsive to the negative pressure within the second chamber for simultaneously increasing the size of the first chamber and reducing the size of the second chamber; and
    means operative after the size of the second chamber has been reduced to a predetermined value for establishing fluid communication between the second chamber and the ambient environment, thereby eliminating the negative pressure within the second chamber.

2. A pulmonary exercising device comprising:
    an axially-extending housing having a top integral with a side wall;
    a base supporting said housing, the side wall of said housing being sealed to said base;
    a hollow tubular member extending between said base and the top of said housing, said tubular member being coaxial with said housing;
    dividing means having a portion thereof positioned for translation on said tubular member for dividing the interior of said housing into a first chamber and a second chamber, at least a portion of the second chamber being positioned above the first chamber;
    first means for establishing fluid communication between the first chamber and the ambient environment;
    second means for establishing fluid communication between the second chamber and a user of the device so that inhalation by the user through the second means creates a negative pressure within the second chamber, said second means including an axially-extending opening formed in an upper portion of said tubular member for establishing fluid communication between the interior of said tubular member and said second chamber, and means for establishing fluid communication between the interior of said tubular member and a user of the device;
    said dividing means having a portion thereof translatable in an upward direction in response to the negative pressure created in said second chamber to simultaneously increase the size of said first chamber and decrease the size of said second chamber; and
    third means operative after the size of the second chamber has been reduced to a predetermined value for establishing fluid communication between the second chamber and the ambient environment, thereby eliminating the negative pressure within the second chamber.

3. A device according to claim 2, wherein said dividing means includes a bushing positioned for translation on said tubular member and a plate member connected to said bushing for dividing said housing into said chambers, and wherein the length of said bushing is less than the length of the opening formed in the upper portion of said tubular member so that said third means is formed when the bottom of said bushing passes the bottom of the opening formed in the upper portion of said tubular member thereby providing fluid communication between said first and said second chambers.

4. A device according to claim 2, wherein said dividing means includes a bushing positioned for translation on said tubular member, means for reducing air flow between said bushing and said tubular member, and a bellows centered on said tubular member and having a closed top end thereof connected to said bushing, the bottom end of said bellows being sealed to one of said base and said side walls so that the interior of said bellows forms said first chamber.

5. A device according to claim 4, wherein said bellows has an outwardly flared lip portion surrounding its bottom end and said side wall terminates at its bottom in an outwardly flared lip portion, said lip portion of said bellows being positioned between said lip portion of said side wall and said base and said lip portions and said base being sealed to each other.

6. A device according to claim 4, wherein the length of said bushing is less than the length of the opening formed in the upper portion of said tubular member so that said third means is formed when the bottom of said bushing passes the bottom of the opening formed in the upper portion of said tubular member thereby providing fluid communication between said first and said second chambers.

7. A device according to claim 3 or claim 6, wherein said base includes a top surface and wall means for supporting the top surface spaced from a surface supporting the device, and wherein said first means comprises a first through opening formed in said wall means, and a second through opening formed in said top surface, said first and said second openings being formed in such manner that fluid communication is established between said first chamber and the ambient environment.

8. A device according to claim 7, wherein said second means comprises a third through opening formed in said top surface, and conduit means for establishing fluid communication between the bottom of said third opening and a user of said device, said third opening being formed in said top surface in such manner that the top of said third opening is surrounded by the bottom of said tubular member with the third opening in fluid communication with the interior of said tubular member.

9. A device according to claim 4, wherein means for urging the closed top end of said bellows towards said base are associated with an upper portion of said bellows.

10. A device according to claim 9, wherein said means for urging comprises a plate member connected to said bushing.

11. A device according to claim 3 or claim 9, wherein the distance between peripheral edges of the plate member and said side wall has a predetermined constant value as the plate member translates within said housing, the distance being selected such that there is substantially no air flow between the peripheral edges and the side wall.

12. A pulmonary exercising device having a first mode of operation in which the device provides a visual indication of the volume of inspired air and a second, subsequent mode of operation in which the device provides a visual indication of the rate of inspiration of air, said device comprising:
a housing;
movable means positioned inside said housing for dividing said housing into first and second chambers;
first means for connecting said first chamber to the ambient environment, said second chamber being separated from said first means by said movable means;
second means for connecting said second chamber to a user of the device so that inspiration of air by the user reduces the pressure in said second chamber, said movable means being responsive to the reduced pressure to increase the size of said first chamber and reduce the size of said second chamber thereby providing a visual indication of the volume of inspired air; and
third means for connecting said second chamber to the ambient environment when the size of said second chamber is reduced to a predetermined volume, said third means when connecting said second chamber to the ambient environment providing a visual indication of the rate of inspiration of air.

13. A device according to claim 12, wherein said third means connects said second chamber to the ambient environment through said first chamber.

14. A device according to claim 12, wherein said movable means is a bellows.

15. A device according to claim 14, wherein said first means comprises openings formed in said housing which communicate with the interior of said bellows.

* * * * *